United States Patent [19]

Matsunaga et al.

[11] Patent Number: 5,702,895
[45] Date of Patent: Dec. 30, 1997

[54] **METHOD AND KIT FOR DETECTING METHICILLIN-RESISTANT *STAPHYLOCOCCUS AUREUS***

[75] Inventors: Hironari Matsunaga; Kenichi Tsukumo; Shinji Wakisaka; Akio Yamane, all of Hiroshima, Japan

[73] Assignee: Wakunaga Seiyaku Kabushiki Kaisha, Osaka, Japan

[21] Appl. No.: 586,274

[22] Filed: Jan. 16, 1996

[30] Foreign Application Priority Data

Jan. 19, 1995 [JP] Japan .................................. 7-006390

[51] Int. Cl.$^6$ .............. C12Q 1/68; C12P 19/34; C07H 21/04; C12N 15/00
[52] U.S. Cl. .............. 435/6; 435/91.1; 435/91.2; 435/810; 435/883; 536/23.7; 536/24.32; 536/24.33; 935/1; 935/8; 935/72; 935/77; 935/78
[58] Field of Search .................. 536/22.1, 23.1, 536/23.7, 24.3, 24.33, 24.32; 435/6, 91.2, 91.1, 183, 810, 883

[56] References Cited

FOREIGN PATENT DOCUMENTS 0 526 876  10/1993  European Pat. Off. .......... C12Q 1/68

OTHER PUBLICATIONS

Ubukata, et al., Rapid Detection of the mecA Gene in Methicillin–Resistant Staphylococci by Enzymatic Detection of the Polymerase Chain Reaction Products, J. Clin. Micro. 30(7):1728–1733, Jul. 1992.

Frenay, H., et al., Discrimination of the Epidemic and Nonepidemic Methicillin Resistant *Staphylococcus aureus* Strains on the Basis of Protein A Gene Polymorphism, J. Clin. Micro. 32(2):846–847, Mar. 1994.

Ryffel, et al., Sequence comparison of the mecA genes isolated from methicillin–resistant *Staphylococcus aureus* and *Staphylococcus epidermidis*, Gene 94:137–138, Aug. 1990.

Uhlen, et al., Complete Sequence of the Staphylococcal Gene Encoding Protein A, J. Biol. Chem. 259(3):1695–1702, Feb. 1984.

*Primary Examiner*—Bradley L. Sisson
*Attorney, Agent, or Firm*—Oblon, Spivak, McClelland, Maier & Neustadt, P.C.

[57] ABSTRACT

A method and a kit for detecting methicillin-resistant *Staphylococcus aureus* which use, as primers in a gene amplification reaction, the four oligonucleotides represented by the following nucleotide sequences (1) through (4):

| | |
|---|---|
| 5'AGAAATGACTGAACGTCCG3' (SEQ ID NO:1) | (1) |
| 5'GCGATCAATGTTACCGTAG3' (SEQ ID NO:2) | (2) |
| 5'TACATGTCGTTAAACCTGGTG3' (SEQ ID NO:3) | (3) |
| 5'TACAGTTGTACCGATGAATGG3' (SEQ ID NO:4) | (4) | wherein A, G, C, and T denote adenine, guanine, cytosine, and thymine, respectively, and any T may be substituted by uracil (U). According to the method and kit of the present invention, it is possible to detect MRSA accurately and rapidly while distinguishing it from MR-CNS. Thus, proper treatment and prevention can be achieved against MRSA infections.

11 Claims, No Drawings

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="COMPLEMENTARY TO THE
            SEQUENCE OF STAPHYLOCOCCUS"

( x i ) SEQUENCE DESCRIPTION: SEQ ID NO:1:

AGAAATGACT GAACGTCCG                                                     19

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="COMPLEMENTARY TO THE
            SEQUENCE OF STAPHYLOCOCCUS"

( x i ) SEQUENCE DESCRIPTION: SEQ ID NO:2:

GCGATCAATG TTACCGTAG                                                     19

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="COMPLEMENTARY TO THE
            SEQUENCE OF STAPHYLOCOCCUS"

( x i ) SEQUENCE DESCRIPTION: SEQ ID NO:3:

TACATGTCGT TAAACCTGGT G                                               21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="COMPLEMENTARY TO THE
            SEQUENCE OF STAPHYLOCOCCUS"

( x i ) SEQUENCE DESCRIPTION: SEQ ID NO:4:

TACAGTTGTA CCGATGAATG G                                               21

( 2 ) INFORMATION FOR SEQ ID NO:5:

( i ) SEQUENCE CHARACTERISTICS:
        ( A ) LENGTH: 20 base pairs (B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:5:

GAAATGACTG AACGTCCGAT                                      20

(2) INFORMATION FOR SEQ ID NO:6:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:6:

GCGATCAATG TTACCGTAGT                                      20

(2) INFORMATION FOR SEQ ID NO:7:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:7:

AGAAATGACT GAACGTCCGA                                      20

(2) INFORMATION FOR SEQ ID NO:8:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:8:

GTAGAAATGA CTGAACGTCC                                      20

(2) INFORMATION FOR SEQ ID NO:9:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:9:

GTTGCGATCA ATGTTACCGT                                      20

(2) INFORMATION FOR SEQ ID NO:10:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: other nucleic acid ( x i ) SEQUENCE DESCRIPTION: SEQ ID NO:10:

CTATGATCCC AATCTAACTT CC 22

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

TAGAAATGAC TGAACGTCCG 20

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

GGTCTTTCTG CATTCCTGG 19

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

TGATGCAATT GAAGATAAAA ATTTC 25

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:14:

TGAATGTTTA TATCTTTAAC GCC 23

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:15:

GCAATTGAAG ATAAAAATTT CAAAC 25

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:16:

GATAGCAGTT ATATTTCTAA AAGC        24

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:17:

ATAATGGTGA AGTAGAAATG ACTGAACGTC        30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:18:

AATTAAATTG AACGTTGCGA TCAATGTTAC        30

( 2 ) INFORMATION FOR SEQ ID NO:19:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:19:

GAAGTTAGAT TGGGATCATA GC        22

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:20:

ACATTCTTTG GAACGATGCC        20

( 2 ) INFORMATION FOR SEQ ID NO:21:

( i ) SEQUENCE CHARACTERISTICS:
        ( A ) LENGTH: 18 base pairs ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:21:

TCGATGGTAA AGGTTGGC                18

( 2 ) INFORMATION FOR SEQ ID NO:22:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:22:

TGTCCGTAAC CTGAATCAGC                20

( 2 ) INFORMATION FOR SEQ ID NO:23:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:23:

CATGTCGTTA AACCTGGTGA T                21

( 2 ) INFORMATION FOR SEQ ID NO:24:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:24:

CAGTTGTACC GATGAATGGA T                21

( 2 ) INFORMATION FOR SEQ ID NO:25:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:25:

AGACTTGAGC ATCTACTCGT T                21

( 2 ) INFORMATION FOR SEQ ID NO:26:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:26:

GTCTAACGAG TAGATGCTCA A                                                                      21

( 2 ) INFORMATION FOR SEQ ID NO:27:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:27:

CGGTGGCGTT AAAGATATAA ACATTCAG                                                               28

( 2 ) INFORMATION FOR SEQ ID NO:28:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:28:

ACCGCTGAAT GTTTATATCT TAACGCC                                                                28

( 2 ) INFORMATION FOR SEQ ID NO:29:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:29:

CGCCGGCGTT AAAGATATAA ACATTCAGGA TC                                                          32

( 2 ) INFORMATION FOR SEQ ID NO:30:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:30:

GGCGGATCCT GAATGTTTAT ATCTTTAACG CC                                                          32

( 2 ) INFORMATION FOR SEQ ID NO:31:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:31:

GCCCAACGAG TAGATGCTCA ATATAAAA                                                               28

( 2 ) INFORMATION FOR SEQ ID NO:32:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:32:

GGGCTTTTAT ATTGAGCATC TACTCGTT                                      28

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:33:

CGTTTAAGAA GCAACCAGCA                                                20

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:34:

AACGTGCTGG TTGCTTCTTA                                                20

( 2 ) INFORMATION FOR SEQ ID NO:35:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:35:

AGCCTGCTAA CAAAGCTCAA GCATTA                                    26

( 2 ) INFORMATION FOR SEQ ID NO:36:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:36:

GGCTTAATGC TTGAGCTTTG TTAGCA                                    26

( 2 ) INFORMATION FOR SEQ ID NO:37:

( i ) SEQUENCE CHARACTERISTICS:
        ( A ) LENGTH: 30 base pairs (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:37:

GCCTTGCTAA CAAAGCTCAA GCATTACCAG                30

(2) INFORMATION FOR SEQ ID NO:38:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:38:

AGGCCTGGTA ATGCTTGAGC TTTGTTAGCA                30

METHOD AND KIT FOR DETECTING METHICILLIN-RESISTANT *STAPHYLOCOCCUS AUREUS*

BACKGROUND OF THE INVENTION i) Field of the Invention

The present invention relates to a method and a kit for detecting methicillin-resistant Staphylococci and particularly methicillin-resistant *Staphylococcus aureus*, microorganisms which are outstanding at coping with infectious diseases.

ii) Description of the Related Art

Methicillin-resistant *Staphylococcus aureus* (hereinafter referred to as MRSA) accounts for not less than 50% of Staphylococci detected by bacteriological examinations in Japan. Special attention must be drawn to MRSA as a causal bacterium for hospital infections. This bacterium is resistant to almost all antibiotics led by beta-lactams, with very few medicines being effective at combatting it. Most antibiotics which are administered for preventive purposes in cases where infectious diseases are suspected are not effective against MRSA. Rather, they may exacerbate the MRSA infection. Therefore, rapid and accurate detection and identification of MRSA in clinical specimens are considered to be critical toward the prevention and treatment of infectious diseases.

MRSA is conventionally identified by culturing bacteria isolated from clinical specimens and checking for the presence of drug sensitivity. Cultivation for this purpose however, requires more than one day for isolating and culturing, and in addition, more than one day for testing sensitivity. Moreover, MRSA's drug resistance is manifested through a complicated mechanism, sometimes causing MRSA to be overlooked when this approach of culture testing is used.

To overcome these drawbacks, an alternative method applying a polymerase chain reaction (hereinafter referred to as PCR; see Japanese Patent Application Laid-open (kokai) No. 60-281) has been developed. According to this method, MRSA is assayed by detecting the mecA gene encoding a novel cell wall synthesizing enzyme, PBP-2', which causes the MRSA's resistance (Ubukata et al., J. Clin. Microbiol. 30, pp. 1728–1733 (1992)). This method is advantageous in that the presence of MRSA can be determined without waiting for the results of antimicrobial susceptibility test, and without being affected by fluctuating factors of cultivation. This method has already been put into practical use.

However, due to the fact that the mecA gene is not necessarily possessed only by *Staphylococcus aureus* but is sometimes also possessed by other Staphylococci such as coagulase-negative Staphylococci (CNS), it is important to distinguish methicillin-resistant CNS (hereinafter referred to as MR-CNS) from MRSA in order to effectively cope with infectious diseases taking account of drug sensitivity. Especially since *Staphylococcus aureus* has stronger toxicity than other Staphylococci, its clinical significance is considered to be greater than that of CNS. Therefore, it is still important to know whether the detected Staphylococcus is *Staphylococcus aureus*. Under these circumstances, it is desired to detect and identify the mecA gene while concurrently distinguishing MRSA from MR-CNS.

PCR is a useful means for detecting and identifying genes rapidly with high sensitivity. Although it is theoretically possible to amplify a gene specific to *Staphylococcus aureus* and the mecA gene in a single reaction by use of PCR, when PCR is actually pursued in one reaction vessel, simple combination of four primers which amplify different genes cannot necessarily result in sufficiently specific gene amplification. That is, when two or more kinds of genes are amplified simultaneously by PCR (multiple PCR), there are observed, with high frequency, nonspecific amplifying reactions involving genes other than the target gene including amplifying reactions of the primers themselves. For example, in performing a PCR reaction using four primers simultaneously, it is naturally essential to design the reaction such that the maceration temperatures (Tm) of the four primers are equal to one another, and such that the sequences in any combination that the four primers can assume are not complementary to one another. However, even when the reaction is carefully designed taking these factors into account, an unexpected decrease in reaction efficiency or production of nonspecific amplified products sometimes occurs (Chamberlain, et al., Nucleic Acid Res., 16, pp. 11141–11156 (1988); Chamberlain et al., PCR Protocols, pp. 272–281, edited by Innis et al., Academic press (1990); Edwards et al., PCR method and Applications 3, pp 565–575 (1994)). Thus, it has been difficult to perform a PCR reaction which is directed to a specific combination of primers.

SUMMARY OF THE INVENTION

Accordingly, a general object of the present invention is to provide, by using a PCR, a rapid and simple method for detecting MRSA while distinguishing it from MR-CNS.

Under the above circumstances, the present inventors studied designs of primers to distinguish MRSA from MR-CNS and to detect MRSA by PCR, and they previously devised to combine two kinds of primers which amplify the mecA gene exhibiting methicillin-resistance and two kinds of primers which amplify the spa gene found in protein A known to be a marker which distinguishes *Staphylococcus aureus* from other Staphylococci (Forsgren, Acta Pathol. Microbiol. Scand. 75, pp. 481–490 (1969); Hjolm et al., FEBS Letters, 28, pp. 73–76). However, in order to achieve a rapid and simple examination, it is necessary that the reaction time in PCR be not too long and that high sensitivity be maintained. To this end, it is desirable to choose a combination of primers from among those combinations which render the length of DNAs obtained after amplification of genes by PCR in the range from 40 to 300 nucleotide bases. In addition, among those combinations, a combination of primers capable of amplifying both genes without causing a nonspecific amplifying reaction must be chosen, which was proved to be very difficult.

The present inventors further conducted research to meet the above-described conditions, and as a result, found that MRSA can be detected as clearly distinguished from MR-NCS if oligonucleotides shown by sequences (1) and (2) below are used as PCR primers which are specific to the mecA gene and oligonucleotides shown by sequences (3) and (4) below are used as PCR primers which are specific to the spa gene (SEQ ID NO:1–4). The present invention was accomplished based on this finding.

Accordingly, the present invention provides a method for detecting methicillin-resistant *Staphylococcus aureus* which comprises a step of using, as reaction primers in a gene amplification reaction, the four oligonucleotides represented by the following nucleotide sequences (1) through (4) (SEQ ID NO:1–4):

5'AGAAATGACTGAACGTCCG3' (SEQ ID NO:1)     (1)

5'GCGATCAATGTTACCGTAG3' (SEQ ID NO:2)     (2)

5'TACATGTCGTTAAACCTGGTG3' (SEQ ID NO:3)     (3)

5'TACAGTTGTACCGATGAATGG3' (SEQ ID NO:4)     (4)

wherein A, G, C, and T denote adenine, guanine, cytosine, and thymine, respectively, and any T may be substituted by uracil (U).

The present invention also provides a kit for detecting methicillin-resistant *Staphylococcus aureus* which includes the above-described four oligonucleotides.

DETAILED DESCRIPTION OF PREFERRED EMBODIMENTS

Among the primers used in the present invention, the oligonucleotides represented by the above nucleotide sequences (1) and (2) (hereinafter referred to as primer (1) and primer (2), respectively) are selected from the mecA gene sequence reported by Matsuhashi at al. [FEBS Letters 221, p. 167–171 (1987)] (SEQ ID NO:1–2). They can be chemically synthesized, for example, by an automated DNA synthesizer. On the other hand, the oligonuleotides represented by the above nucleotide sequences (3) and (4) (hereinafter referred to as primer (3) and primer (4), respectively) are selected from the spa gene sequence reported by Finck-Barbancon et al. [FEMS Microbiol. Lett. 91, pp. 1–8 (1992)] (SEQ ID NO:3–4). They can be chemically synthesized, for example, by an automated DNA synthesizer.

According to the method for detecting MRSA of the present invention, a routine PCR method is used except that the aforementioned four kinds of primers are used in combination. In more detail, the method of the present invention includes several tens of cycles each cycle consisting of denaturation to a single-stranded DNA, annealing, and elongation, with the above four primers and polymerase being applied to a specimen and detecting the resultant amplified genes.

Specimens used in the present invention include, but are not limited to, a variety of clinical examination specimens, blood, pus, sputum, spinal fluid, throat swab, stools, and urine; bacterial cultures obtained with these materials; and isolated and cultured bacterial colonies. In order to perform an examination, nucleic acid components of Staphylococci which serve as specimens undergoing PCR must be extracted from these materials. This can be accomplished by a method which uses an alkaline substance or a detergent. Alternatively, a method using a protease such as proteinase K may also be employed. When enzymes which lyse membranes characteristic to Staphylococci such as lysostaphin and achromopeptidase are used, these enzymes enhance efficiency of extracting nucleic acids and elevate sensitivity of the examination.

A portion of a solution containing a nucleic acid extract may be directly used in PCR. It is also possible to elevate sensitivity of PCR by including steps such as purification and concentration of nucleic acid. Examples of the methods to perform purification or concentration include a method in which an organic solvent such as phenol is used as a denaturing agent for a protein, a method in which other specific protein-denaturing agents are used (Beutler et al., BioTechniques 9, p. 166 (1990)), and a method in which carriers such as latex particles to which probes for capturing and concentrating are used (Japanese Patent Application Laid-open (kokai) No. 63-117262).

As a polymerase used in PCR, a heat resistant DNA polymerase such as Taq DNA polymerase is preferably used. The treatment to denature into a single-stranded DNA is preferably a thermal treatment. Preferred PCR conditions are, for example, those including a denaturing step using a heat-resistant DNA polymerase under thermal cycle conditions of 90°–96° C. for 10–60 seconds, more preferably at 92° C. for 15 seconds, an annealing step at 50°–65° C. for 10–60 seconds, more preferably at 60°–65° C. for 15 seconds, and an elongation step at 72° C. for 0 to 60 seconds, more preferably, for 5–15 seconds.

The amplification of DNA by a PCR using primers of the present invention may be determined by a method in which the size of the amplified DNA is confirmed by electrophoresis, or by a method in which the reaction products are immobilized onto a membrane such as a nitrocellulose membrane, followed by hybridization with a labelled probe having a sequence complementary to the sequence of the target amplified DNA. However, it is advantageous to use an easier method to determine the amplification of DNA, in which primers with discernible labelling are used in PCR and the amplified DNA which has been labelled is captured by a solid phase and discerned.

There are several methods for capturing and determining amplified DNA. One method employs a solid phase to which a substance capable of being specifically bound to a label is immobilized in advance (Japanese Patent Application Laid-open (kokai) No. 1-252300). In another method, a capturing probe having a sequence complementary to the sequence of the target amplified DNA is immobilized onto a solid phase in advance, and specific binding is achieved by hybridization. The solid phase may be a microtiter well, beads, etc. In order to process many specimens simultaneously, it is advantageous to use a microtiter well.

When a clinical specimen is directly used as a sample to be examined, the number of Staphylococci contained therein may be small if it is present. In such cases, a thermal treatment cycle may have to be repeated many times to amplify DNA in PCR. Under such situations, use of primers obtained after careful studies cannot completely remove the risk of nonspecific amplified DNA occurring. Therefore, to capture amplified DNA, it is advisable to use hybridization with a capturing probe. To immobilize a capturing probe onto a microtiter well, a method proposed by Kawai et al. may be used (Analytical Biochemistry 209, pp. 63–69).

EXAMPLES

The present invention will next be described in more detail by way of examples, which should not be construed as limiting the invention.

Example 1

Selection of primers (1) Preparation of a specimen

A methicillin-resistant *Staphylococcus aureus* strain TK784 and *E. Coli* were independently cultured in a Mueller-Hinton medium. DNA was prepared by extraction using SDS-phenol.

(2) Synthesis and labelling of primers

The oligonucleotides to be used as primers were synthesized by a phosphoamidide method using a DNA synthesizer (Applied Biosystems), obtaining primers (M1–M12) for amplifying the mecA gene and primers (S1–S4) for amplifying the spa gene which were designed based on the sequences of the respective genes (SEQ ID NO:1–24). An amino group was introduced to the 5'-terminal using an aminolink II (trademark, product of Applied Biosystems), and then the resultant amino-introduced oligonucleotide was purified by gel filtration using Sephadex G-50.

The amino-introduced oligonucleotides were labelled by the following method. In a solution containing 10 µg/µl DMF and 100 mM NaHCO₃, an amino-introduced oligonucleotide was allowed to react with a biotinyl-N-hydroxysuccinimide ester, obtaining a biotin-labelled oligonucleotide. Alternatively, in a solution containing 33% ethanol and 67 mM NaHCO₃, an amino-introduced oligonucleotide was allowed to react with dinitrofluorobenzene, obtaining a dinitrophenyl-labelled oligonucleotide.

(3) PCR

A PCR was performed placing a reaction liquid containing a DNA specimen (20 ng), the four primers (a pair of primers for amplifying the mecA gene and a pair of primers for amplifying the spa gene: each 50 ng/50 µl), Taq DNA polymerase (2.5 units/50 µl), 200 µM each of dATP, dGTP, and dCTP, 400 µM of dUTP, 50 mM of KCl, and 50 mM of Tris buffer (pH 8.3) in a thermal cycler 9600 (Perkin Elmer-Cetus). A PCR cycle consisting of a denaturing step at 92° C. for 15 seconds, an annealing step at 60° C. for 15 seconds, and an elongation step at 72° C. for 15 seconds was repeated 40 times.

The primers for amplifying the mecA gene (M1, M2, M3, M4, M5, M6, M7, M8, M9, M10, M11, and M12) and those for amplifying spa gene (S1, S2, S3, and S4), all shown in Table 1, were added in combinations as shown in Table 2 (SEQ ID NO:1–24). The odd numbers indicate sequences corresponding to the sense side of the gene, and the even numbers indicate sequences corresponding to the antisense side. To the sequences indicated by odd numbers present on the side which is to undergo investigation of amplification efficiency, biotin-labelled oligonucleotide primers were applied. In addition, to the sequences indicated by even numbers on the same side, dinitrophenyl-labelled oligonucleotide primers were applied. To the sequences on the other side were applied amino-introduced oligonucleotide primers.

(4) Determination of the results of amplification

Amplification of genes by PCR was determined as follows. 10 µl of each reaction liquid which underwent amplification and 100 µl of an alkaline phosphatase-labelled anti-dinitrophenyl antibody solution were added in a streptoavidin-immobilized microtiter well and incubated at 25° C. for 30 minutes. After washing, 100 µl of a p-nitrophenylphosphoric acid solution (40 µg/ml) were added and incubated at 25° C. for 30 minutes. Absorbance at 405 nm was measured using a microplate reader.

(5) Results

As shown in Table 2, when MRSA DNA was added, strong colorations of not less than 1.0 were observed. After *E. coli* DNA was added, a combination of primers M9 (SEQ ID NO:1), M6 (SEQ ID NO:2), S3 (SEQ ID NO:3), and S4 (SEQ ID NO:4) provided nonspecific coloration of not more than 0.1.

TABLE 1

Primers for detecting the mecA gene

| | |
|---|---|
| M1: | 5' GAAATGACTGAACGTCCGAT 3' (SEQ ID NO:5) |
| M2: | 5' GCGATCAATGTTACCGTAGT 3' (SEQ ID NO:6) |
| M3: | 5' AGAAATGACTGAACGTCCGA 3' (SEQ ID NO:7) |
| M6: | 5' GCGATCAATGTTACCGTAG 3' (Sequence No. 2) |
| M7: | 5' GTAGAAATGACTGAACGTCC 3' (SEQ ID NO:8) |
| M8: | 5' GTTGCGATCAATGTTACCGT 3' (SEQ ID NO:9) |
| M9: | 5' AGAAATGACTGAACGTCCG 3' (Sequence No. 1) |
| M10: | 5' CTATGATCCCAATCTAACTTCC 3' (SEQ ID NO:10) |
| M11: | 5' TAGAAATGACTGAACGTCCG 3' (SEQ ID NO:11) |
| M12: | 5' GGTCTTTCTGCATTCCTGG 3' (SEQ ID NO:12) |
| M13: | 5' TGATGCAATTGAAGATAAAAATTTC 3' (SEQ ID NO:13) |
| M14: | 5' TGAATGTTTATATCTTTAACGCC 3' (SEQ ID NO:14) |
| M15: | 5' GCAATTGAAGATAAAAATTTCAAAC 3' (SEQ ID NO:15) |
| M16: | 5' GATAGCAGTTATATTTCTAAAAGC 3' (SEQ ID NO:16) |
| M17: | 5' ATAATGGTGAAGTAGAAATGACTGAACGTC 3' (SEQ ID NO:17) |
| M18: | 5' AATTAAATTGAACGTTGCGATCAATGTTAC 3' (SEQ ID NO:18) |
| M19: | 5' GAAGTTAGATTGGGATCATAGC 3' (SEQ ID NO:19) |
| M20: | 5' ACATTCTTTGGAACGATGCC 3' (SEQ ID NO:20) |
| M21: | 5' TCGATGGTAAAGGTTGGC 3' (SEQ ID NO:21) |
| M22: | 5' TGTCCGTAACCTGAATCAGC 3' (SEQ ID NO:22) |

Primers for detecting the spa gene

| | |
|---|---|
| S1: | 5' CATGTCGTTAAACCTGGTGAT 3' (SEQ ID NO:23) |
| S2: | 5' CAGTTGTACCGATGAATGGAT 3' (SEQ ID NO:24) |
| S3: | 5' TACATGTCGTTAAACCTGGTG 3' (Sequence No. 3) |
| S4: | 5' TACAGTTGTACCGATGAATGG 3' (Sequence No. 4) |

TABLE 2

| mecA primer | | | | spa primer | | | | MRSA DNA 20 ng | E. coli DNA 20 ng |
| --- | --- | --- | --- | --- | --- | --- | --- | --- | --- |
| primer (1) | label | primer (2) | label | primer (3) | label | primer (4) | label | | |
| M5 | Biotin | M6 | DNP | S1 | None | S2 | None | 1.1 | 0.65 |
| M5 | Biotin | M6 | DNP | S3 | " | S4 | " | 1.17 | 0.6 |
| M5 | Biotin | M10 | DNP | S1 | " | S2 | " | 0.53 | 0.02 |
| M5 | Biotin | M10 | DNP | S3 | " | S4 | " | 0.56 | 0.02 |
| M5 | Biotin | M12 | DNP | S1 | " | S2 | " | 0.44 | 0.04 |
| M5 | Biotin | M12 | DNP | S3 | " | S4 | " | 0.38 | 0.03 |
| M9 | Biotin | M6 | DNP | S1 | " | S2 | " | 1.57 | 0.09 |
| M9 | Biotin | M6 | DNP | S3 | " | S4 | " | 1.64 | 0.1 |
| M9 | Biotin | M10 | DNP | S1 | " | S2 | " | 0.79 | 0.15 |
| M9 | Bitoin | M10 | DNP | S3 | " | S4 | " | 0.69 | 0.2 |
| M9 | Biotin | M12 | DNP | S1 | " | S2 | " | 0.95 | 0.44 |
| M9 | Biotin | M12 | DNP | S3 | " | S4 | " | 0.82 | 0.5 |
| M11 | Biotin | M6 | DNP | S1 | " | S2 | " | 1.52 | 0.40 |
| M11 | Biotin | M6 | DNP | S3 | " | S4 | " | 1.35 | 0.36 |
| M11 | Biotin | M10 | DNP | S1 | " | S2 | " | 0.74 | 0.12 |
| M11 | Biotin | M10 | DNP | S3 | " | S4 | " | 0.6 | 0.1 |
| M11 | Biotin | M12 | DNP | S1 | " | S2 | " | 0.59 | 0.15 |
| M11 | Biotin | M12 | DNP | S3 | " | S4 | " | 0.52 | 0.11 |
| M9 | None | M6 | None | S1 | Biotin | S2 | DNP | 1.47 | 0.15 |
| M9 | None | M6 | None | S3 | Biotin | S4 | DNP | 1.1 | 0.02 |

Example 2
Recognition of the specificity of the spa gene
(1) Specimen

Colonies of clinically isolated Staphylococci (Staphylococci aureus: 187 strains, other Staphylococcus strains (CNS): 25 strains) were used as specimens.

(2) PCR

A portion of a specimen colony (corresponding to $10^5$–$10^7$ bacteria) was suspended in 30 µl of a bacteriolysing solution 1 (7 µg/30 µl of lysostaphin and 50 mM of Tris buffer (pH 7.5)), and incubated at 50° C. for 5 minutes. Thereafter, 10 µl of a bacteriolysing solution 2 (2 µg/10 µl of proteinase K, 110 mM Tris buffer (pH 8.9), 1.5 mM $MgCl_2$, 80 mM KCl, and 50 µg/10 µl of bovine serum albumin) were added, followed by incubations at 60° C. for 10 minutes and then at 94° C. for 5 minutes. To the resultant mixture, a reagent for amplification (primers S3 and S4 for amplifying the spa gene (50 ng/10 µl each), Taq DNA polymerase (2.5 units/10 µl ), 10 nmole/10 µl each of dATP, dGTP, dCTP, and dTTP, 250 mM KCl, and 250 mM of Tris buffer (pH 8.3)) was added and the PCR procedure of Example 1 was repeated (SEQ ID NO:3–4).

(3) Determination of the results of amplification

In a manner similar to that described in Example 1, amplification of gene was determined using a streptoavidin-immobilized well and an alkaline phosphatase-labelled anti-dinitrophenyl antibody solution.

(4) Results

After PCR, it was found that all the 187 Staphylococcus aureus strains were spa gene positive. In addition, as regards other Staphylococci strains, no amplification of spa gene was observed.

Example 3
Detection of amplification using probes
(1) Preparation of a phage probe-immobilized microtiter well Probe oligonucleotides (M13, M14, M17, M18, M19, M20, M21, M22, S13, S14, S17, S18, S19, S20, S21, S22, S23, and S24) were synthesized with a DNA synthesizer (Applied Biosystems) in a manner similar to that described in Example 1 by adding, to probes for the mecA gene and those for the spa gene shown in Table 3 which were designed based on the sequence of the respective genes, sequences for ligation (in Table 3, sequences for ligation are indicated by small letters) (SEQ ID NO:25–38). In each complementary combination of oligonucleotides (M13 and M14, M17 and M18, M19 and M20, M21 and M22, S13 and S14, S17 and S18, S19 and S20, S21 and S22, S23 and S24), 10 oligonucleotides were serially ligated using a DNA ligase (SEQ ID NO:25–38). Each of the ligated oligonucleotides was then inserted into a plasmid pUCSfi. Using the plasmids, an E. coli strain JM 109 was transformed. The transformed E. coli strains were cultured, after which helper phages were added to obtain single-stranded DNAs having target probe sequences, MP14 (containing the sequence of M14), MP17 (containing the sequence of M17), MP19 (containing the sequence of M19), MP21 (containing the sequence of M21), SP13 (containing the sequence of S13), SP21 (containing the sequence of S21), and SP23 (containing the sequence of S23) (SEQ ID NO:26 , 27, 29, 31, 33, 35, 37). Each single-stranded DNA (hereinafter referred to as a phage probe) thus obtained was diluted to a concentration of 100 ng/µl using Tris buffer (pH 7.6, supplemented with 1 mM of EDTA). One volume of the resultant solution was mixed with 4 volumes of $H_2O$ and 5 volumes of an immobilizing buffer (1.5M NaCl, 0.3M Tris.HCl (pH 8.0), and 0.3M of $MgCl_2$). The mixture was added to the wells of a microtiter (Glyner) in amounts of 100 µl per well. The top of each well was covered with a lid, and the wells were allowed to stand for 16 hours at 37° C. Subsequently, the liquid was removed and then dried by applying air.

TABLE 3

Probes for the mecA gene

M13: 5' agacTTGAGCATCTACTCGTT 3' (SEQ ID NO:25)
M14: 5' gtctAACGAGTAGATGCTCAA 3' SEQ ID NO:26)
M17: T' cggtGGCGTTAAAGATATAAACATTCAG 3' (SEQ ID NO:27)
M18: 5' accgCTGAATGTTTATATCTTTAACGCC 3' (SEQ ID NO:28)
M19: 5' cgccGGCGTTAAAGATATAAACATTCAGGATC 3' (SEQ ID NO:29)
M20: 5' ggcgGATCCTGAATGTTTATATCTTTAACGCC 3' (SEQ ID NO:30)
M21: 5' gcccAACGAGTAGATGCTCAATATAAAA 3' (SEQ ID NO:31)
M22: 5' gggcTTTTATATTGAGCATCTACTCGTT 3' (SEQ ID NO:32)

Probes for the spa gene

S13: 5' cgttTAAGAAGCAACCAGCA 3' (SEQ ID NO:33)
S14: 5' aacgTGCTGGTTGCTTCTTA 3' (SEQ ID NO:34)
S21: 5' agccTGCTAACAAAGCTCAAGCATTA 3' (SEQ ID NO:35)
S22: 5' ggctTAATGCTTGAGCTTTGTTAGCA 3' (SEQ ID NO:36)
S23: 5' gcctTGCTAACAAAGCTCAAGCATTACCAG 3' (SEQ ID NO:37)
S24: 5' aggcCTGGTAATGCTTGAGCTTTGTTAGCA3' (SEQ ID NO:38)

(2) Detection using phage probe-immobilized microtiter wells PCR:

In a manner similar to that described in Example 1, PCR was performed using the DNA of MRSA as a specimen. M9, M6, S3 and S4 which had been labelled with biotin were used as primers. (Ser ID NO:1-4)

To 50 μl of a reaction liquid which had undergone gene amplification reaction, 50 μl of a 0.4N NaOH solution was added to denature the DNA. Subsequently, the mixture was neutralized by adding 50 μl of 0.4N HCl. Thirty μl of the neutralized solution were added to each phage probe-immobilized microtiter well to which 100 μl of a hybridization buffer (500 mM Tris.HCl (pH 7.5), 100 mM NaCl, and 13% guanidine thiocyanic acid) were added in advance. The content of the wells were incubated for 1 hour at 37° C. After removing liquids, the wells were washed with a washing solution (0.1 M Tris·HCl (pH 7.5), 0.3M NaCl, 2 mM $MgCl_2$, and 0.05% Triton-X 100) twice. An alkaline phosphatase-labelled streptoavidin solution (100 μl) was then added followed by incubation for 15 minutes at 37° C. A washing solution was applied and washing was performed twice. A p-nitrophenyl phosphoric acid solution (40 μg/ml, 100 μl) was added and incubation for 30 minutes at 37° C. followed. Absorbance at 405 nm was measured using a microplate reader.

(3) Results

As is shown in Table 4, all the phage probe-immobilized wells were usable for capturing amplified genes.

TABLE 4

| Phage probe | Absorbance (405 nm) |
|---|---|
| MP13 | 0.815 |
| MP17 | 0.719 |
| MP19 | 0.537 |
| MP21 | 0.649 |
| SP13 | 0.724 |
| SP21 | 0.427 |
| SP23 | 0.853 |

Example 4

Confirmation of the specificity:

(1) Preparation of a specimen

The following bacteria were cultured in a manner similar to that described in Example 1 to prepare DNAs. Staphylococcus aureus TK784 (MRSA), Staphylococcus aureus ATCC 19636 (MSSA), Staphylococcus epidermidis No. 86 (methicillin-resistant strain: MRSE), Staphylococcus epidermidis TK3344N (methicillin-sensitive: MSSE), Echerichia coli, Citrobacter freundi, Klebsiella pneumoniae, Salmonella typhimurium, Enterobacter cloacae, Proteus mirabills, Morganella morgani, Providencia rettgeri, Pseudomonas aeruginosa, and Acinetobacter calcoaceticus.

(2) Detection

The PCR procedure described in Example 1 was repeated except that a combination of primers M9 (SEQ ID NO:1), M6 (SEQ ID NO:2), S3 (SEQ ID NO:3), and S4 (SEQ ID NO:4) described in Example 1 was used.

For detection, microtiter wells were used to which a single-stranded DNA, MP 21, and another single-stranded DNA, SP 23, shown in Example 3 were immobilized. The hybridization method and color detection were the same as described in Example 3.

(3) Results

As is shown in Table 5, coloration was specifically observed on strains which conserved mecA and spa. Strains which do not have these genes did not exhibit coloration. Thus, it was confirmed that the method of the present invention is capable of specifically detecting MRSA.

TABLE 5

| Specimen | Absorbance (405 nm) | | | |
|---|---|---|---|---|
| | MP21 (mecA) | | SP23 (spa) | |
| Staphylococcus aureus (MRSA) | >3.00 | 2.64 | 2.17 | 2.15 |
| Staphylococcus aureus (MSSA) | 0.02 | 0.02 | >3.00 | >3.00 |
| Staphylococcus epidermidis (MRSE) | 0.83 | 0.76 | 0.00 | 0.00 |
| Staphylococcus epidermidis (MSSE) | 0.00 | 0.00 | 0.01 | 0.00 |
| Eschericia coli | 0.01 | 0.01 | 0.01 | 0.01 |
| Citrobacter freundii | 0.02 | 0.01 | 0.01 | 0.01 |
| Klebsiella pneumoniae | 0.00 | 0.01 | 0.01 | 0.01 |
| Salmonella typhimurium | 0.01 | 0.01 | 0.01 | 0.00 |
| Enterobacter cloacae | 0.02 | 0.01 | 0.01 | 0.01 |
| Proteus mirabilis | 0.03 | 0.01 | 0.01 | 0.00 |
| Morganella morgani | 0.00 | 0.05 | 0.00 | 0.01 |
| Providencia rettgeri | 0.01 | 0.01 | 0.01 | 0.00 |
| Psuedomonas aeruginosa | 0.01 | 0.01 | 0.01 | 0.01 |
| Acinetobacter calcoaceticus | 0.01 | 0.01 | 0.08 | 0.01 |

As described above, when the detection method of the present invention is used, it is possible to detect MRSA accurately and rapidly while distinguishing it from MR-CNS. Thus, proper treatment and prevention can be achieved against MRSA infections.

What is claimed is:

1. A method for detecting methicillin-resistant *Staphylococcus aureus* (MRSA) from a DNA specimen, which comprises:

a) obtaining an isolated DNA specimen wherein said DNA specimen is suspected of containing mecA and spa gene sequences;

b) combining said DNA specimen with four primers wherein said primers have the nucleotide residue sequence set forth in SEQ ID NO: 1, SEQ ID NO:2, SEQ ID NO:3, and SEQ ID NO:4;

c) subjecting the combined DNA specimen and four primers to conditions which permit specific amplification of the mecA and spa gene sequences;

d) detecting the presence of the amplified nucleic acid sequences wherein the presence of both amplification products is indicative of MRSA.

2. The method of claim 1, wherein said reaction comprises:

i) denaturing said DNA in the presence of a heat-stable DNA polymerase at about 90°–96° C. for about 10–60 seconds;

ii) annealing at about 50°–65° C. for about 10–60 seconds; and iii) elongating at about 72° C. for about 0–60 seconds.

3. The method of claim 2, wherein said heat-stable DNA polymerase is Taq DNA polymerase.

4. The method of claim 1, wherein at least one of said nucleotide detection primers is labeled at the 3'- or 5'-terminus.

5. The method of claim 4, wherein the 5'-terminus is labeled with biotin or dinitrobenzene.

6. The method of claim 1, wherein said extracting step comprises treating said specimen with a reagent selected from the group consisting of an alkaline substance, detergent, protease, lysostaphin and achromopeptidase.

7. The method of claim 1, wherein said purifying step comprises extracting said DNA with a protein-denaturing agent.

8. The method of claim 1, wherein said isolating step comprises immobilizing the amplified DNA on a membrane and said determining step is effected by hybridizing thereto a labeled oligonucleotide comprising a sequence complementary to the immobilized DNA.

9. A kit, comprising the four nucleotide detection primers:

| | |
|---|---|
| 5'-AGAAATGACTGAACGTCCG-3' (SEQ ID NO:1), | (1) |
| 5'-GCGATCAATGTTACCGTAG-3' (SEQ ID NO:2), | (2) |
| 5'-TACATGTCGTTAAACCTGGTG-3' (SEQ ID NO:3), | (3) | and

| | |
|---|---|
| 5'-TACAGTTGTACCGATGAATGG-3' (SEQ ID NO:4) | (4) | wherein A, G, C and T denote adenine, guanine, cytosine and thiamine, respectively, and any T may be substituted by uracil (U).

10. The kit of claim 9, which further comprises one or more enzymes which lyse membranes of Staphylococci.

11. The kit of claim 10, wherein said one or more enzymes are selected from the group consisting of lysostophin and achromopeptidase.

* * * * *